(12) United States Patent
Li et al.

(10) Patent No.: US 8,106,196 B2
(45) Date of Patent: Jan. 31, 2012

(54) DIHYDROPYRIMIDINE COMPOUNDS AND THEIR USES IN MANUFACTURE OF A MEDICAMENT FOR TREATMENT AND PREVENTION OF VIRAL DISEASES

(75) Inventors: Song Li, Beijing (CN); Xuejun Zhu, Beijing (CN); Guoming Zhao, Beijing (CN); Lili Wang, Beijing (CN); Wu Zhong, Beijing (CN); Zhibing Zheng, Beijing (CN); Junhai Xiao, Beijing (CN)

(73) Assignee: Beijing Molecule Science and Technology Co., Ltd, Beijing (CN)

( * ) Notice: Subject to any disclaimer, the term of this patent is extended or adjusted under 35 U.S.C. 154(b) by 12 days.

(21) Appl. No.: 12/523,292

(22) PCT Filed: Jan. 3, 2008

(86) PCT No.: PCT/CN2008/000022
§ 371 (c)(1),
(2), (4) Date: Aug. 25, 2009

(87) PCT Pub. No.: WO2008/086729
PCT Pub. Date: Jul. 24, 2008

(65) Prior Publication Data
US 2010/0010013 A1    Jan. 14, 2010

(30) Foreign Application Priority Data
Jan. 16, 2007 (CN) .......................... 2007 1 0000688

(51) Int. Cl.
*C07D 405/04* (2006.01)
*C07D 409/04* (2006.01)
*A61K 31/496* (2006.01)

(52) U.S. Cl. ........................................ 544/333; 514/256
(58) Field of Classification Search .................. 544/333; 514/256
See application file for complete search history.

(56) References Cited

FOREIGN PATENT DOCUMENTS
WO     9901438 A1    1/1999

OTHER PUBLICATIONS

Goff, PubMed Abstract (J Gene Med 3(6):517-28), Nov.-Dec. 2001.*
Bosseray et al., PubMed Abstract (Pathol Biol (Paris) 50(8):483-92), Oct. 2002.*
Razonable et al., PubMed Abstract (Herpes 10(3):60-5), Dec. 2003.*
Douglas, Jr. Introduction to Viral Diseases, Cecil Textbook of Medicine, 20th Edition, vol. 2, pp. 1739-1747, 1996.*
Ulrich, Chapter 4:Crystallization, Kirk-Othmer Encyclopedia of Chemical Technology, Aug. 2002.*
Vippagunta et al., Crystalline Solids, Advanced Drug Deliversy Reviews, 48, pp. 3-26, 2001.*
West, Solid Solutions, Solid State Chemistry and its applications, pp. 358 & 365, 1988.*
International Search Report for PCT/CN2008/000022, mailed on Mar. 27, 2008.
Lengar et al., Tunable Carbon-Carbon and Carbon-Sulfur Cross Coupling of Boronic Acids with 3,4-Dihydropyrimidine-2-thiones, Organic Letters, vol. 6, No. 5, 2004, pp. 771-774.
Chinese Office Action dated Jul. 19, 2010 for Appln. No. 2008880000937.1.
Chinese Office Action dated Oct. 9, 2010 for Appln. No. 2008880000937.1.
Chinese Office Action dated Jan. 10, 2011 for Appln. No. 2008880000937.1.
Lengar et al.; "Tunable Carbon-Carbon and Carbon-Sulfur Cross-Coupling of Boronic Acids with 3, 4-Dihydropyrimidine-2-Thiones"; Organic Letters, vol. 6, No. 5, pp. 771-774; Dec. 23, 2003.

* cited by examiner

*Primary Examiner* — Deepak Rao
(74) *Attorney, Agent, or Firm* — Pillsbury Winthrop Shaw Pittman, LLP

(57) ABSTRACT

The present invention relates to compounds of the formula (I) or pharmaceutically acceptable salts or hydrates thereof. The present invention further relates to processes for the preparation of the compounds of formula (I) and optical isomers and to use of the compounds of formula (I), isomers, pharmaceutically acceptable salts or hydrates thereof as medicaments, in particular as medicaments for the treatment and prevention of Hepatitis B.

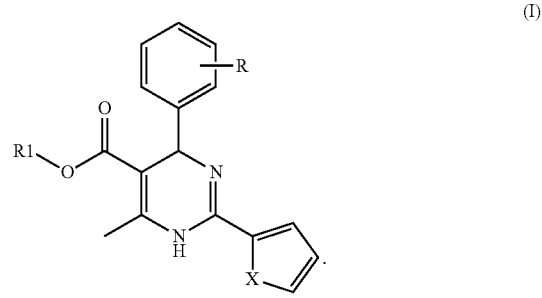

(I)

2 Claims, No Drawings

DIHYDROPYRIMIDINE COMPOUNDS AND THEIR USES IN MANUFACTURE OF A MEDICAMENT FOR TREATMENT AND PREVENTION OF VIRAL DISEASES

CROSS REFERENCE TO RELATED APPLICATIONS

This is the U.S. National Phase of PCT/CN2008/000022, filed Jan. 3, 2008, which claims priority to Chinese patent application No. 200710000688.3, filed Jan. 16, 2007, both of which are incorporated by reference herein in their entireties.

TECHNICAL FIELD

The present invention relates to a dihydropyrimidine compound of the formula (I), a process for the preparation of the compound, a pharmaceutical composition comprising the compound, and the use of the compound, a isomer, a pharmaceutically acceptable salt or a hydrate thereof as a medicament, in particular as a medicament for the treatment and prevention of Hepatitis B.

BACKGROUND ART

Chronic Hepatitis B is a severe infectious disease caused by hepatitis B virus (HBV), widely prevalent throughout the world, and is closely associated with the occurrence of hepatocirrhosis and liver cancer. China belongs to a high prevalence area of Hepatitis B. The results of nationally seropidemiological survey of viral hepatitis in China from 1992 to 1995 showed that the persons carrying viral hepatitis B surface antigen (HBsAg) in China accounted for 9.7% of the population, and it was estimated that there are $1.3 \times 10^8$ HBV carriers. The study on the epidemic situation of viral hepatitis in China showed that the annual reported incidence of hepatitis B as increased from 21.9/100 thousands in 1990 to 53.3/100 thousands in 2003, which exhibited an obvious ascending trendency (see, Wang Xiaojun, Zhang Rongzhen and Hu Yuansheng et al, Disease Monitoring, 2004, 19(8): 290-292). Chronic Hepatitis B not only seriously affects the human health but also imposes heavy economic burden on family and society. Chronic Hepatitis B has become one of the significant public health problems in China.

There are main two classes of drugs useful for the treatment of Chronic Hepatitis B, i.e. immunomodulators and nucleoside DNA polymerase inhibitors (Loomba R., Liang T. J., Antivir. Ther., 2006, 11(1): 1-15), wherein the former includes interferon-α2b (IFN-α2b, Intron A®), and pegylated interferon-α2a (peg-IFN-α2a, Pegasys®); and the latter includes Lamivudine (EPivir-HBV®), Adefovir Dipivoxil (Hepsera®) and Entecavir (Baraclude®). Comparatively speaking, there are limited drugs for the clinical treatment of Hepatitis B in the terms of its number and class. Therefore, it is of significance to continuously research and develop of novel, safe and effective antiviral drugs, in particular those having a totally new mechanism of action.

Deres et al reported the dihydropyrimidine (HAP) compounds substituted by a heteroaryl ring with Bay41-4109 and Bay36-5493 as representatives, which compounds can inhibit HBV replication by blocking the normal formation of nucleocapsids. The pre-clinical data showed that Bay41-4109 has good drug pharmacokinetic parameters (Deres K., Schroder C. H., Paessens A., et al, Science, 2003, 299 (5608): 893-896). The study on their mechanism of action showed that HAP changed the included angle between the dimers for forming the nucleocapsid by interacting with amino residues 113-143 of the core protein, resulting in formation of an unstable and expanded nucleocapsid to accelerate the degradation of the core protein (Hacker H. J., Deres K., Mildenberger M., et al., Biochem. Pharmacol., 2003, 66(12): 2273-2279).

THE CONTENTS OF THE INVENTION

The present invention relates to a dihydropyrimidine compound of the formula (I),

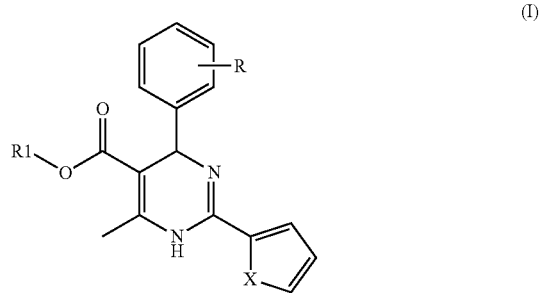

wherein

R represents one or more occurrences of identical or different substituents selected from the group consisting of hydrogen, halogen, trifluoromethyl, trifluoromethoxy, trifluoromesyl, nitro, cyano, carboxyl, hydroxyl, ($C_1$-$C_6$)-alkoxy, ($C_1$-$C_6$)-alkoxycarbonyl or ($C_1$-$C_6$)-alkyl, $R^1$ represents a ($C_1$-$C_6$)-alkyl group, and X represents oxygen or sulfur, a isomer, a pharmaceutically acceptable salt, or a hydrate thereof.

In the specification of the present application, the term "($C_1$-$C_6$)-alkyl" represents a straight-chain or branched radical having 1 to 6 carbon atoms, which includes but is not limited to methyl, ethyl, n-propyl, iso-propyl, n-butyl, sec-butyl, iso-butyl, tert-butyl or the like.

In the specification of the present application, the term "($C_1$-$C_6$)-alkoxy" represents a straight-chain or branched alkoxy having 1 to 6 carbon atoms, preferably having 1 to 4 carbon atoms, which includes but is not limited to methoxy, ethoxy, propoxy, iso-propoxy, butoxy, iso-butoxy or tert-butoxy or the like.

In the specification of the present application, the term "($C_1$-$C_6$)-alkoxycarbonyl" represents a straight-chain or branched alkoxycarbonyl having 1 to 6 carbon atoms, preferably having 1 to 4 carbon atoms, which includes but is not limited to methoxycarbonyl, ethoxycarbonyl, propoxycarbonyl, iso-propoxycarbonyl, butoxycarbonyl, iso-butoxycarbonyl, tert-butoxycarbonyl or the like.

The compounds of the present application include a compound of the general formula (I) and an isomer thereof (Ia) and mixtures thereof. The isomers (I) and (Ia) may exist in a tautomeric equilibrium:

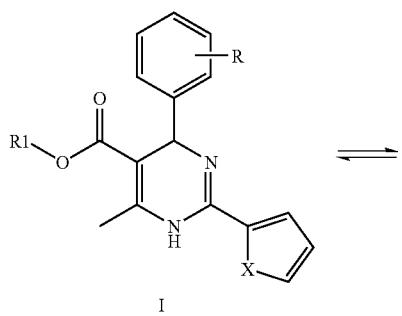

I

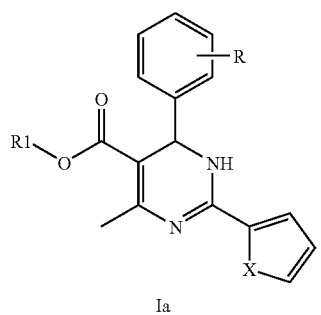

Ia

The compounds according to the present invention may exist in the form of optical isomers which are in relationship of enantiomers or diastereomers. The present invention relates to such enantiomers or diastereomers and their mixtures. The racemate can, like the diasteromers, be resolved in a known manner into a single component of the isomers. For example, another chiral group is introduced into the molecule of the present compound to form a pair of diastereomers which are easy to be separated, and the optically pure enantiomers are obtained by removing the introduced chiral group after separation and purification.

The chiral group may be introduced by the following processes.

Process [A] Comprising 1) reacting a compound of the formula general (I) with an anhydride or chloride of an acid containing at least one chiral center in its molecule in an appropriate inert solvent with the addition of a baser or reacting a compound of the formula general (I) with an acid containing at least one chiral center in its molecule in the presence of an appropriate condensing agent, to obtain a compound of the general formula (VII) or (VIII)

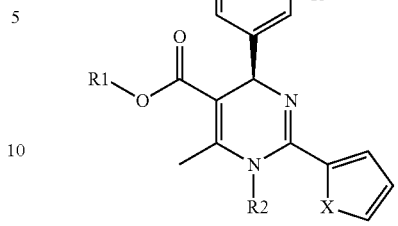

(VII)

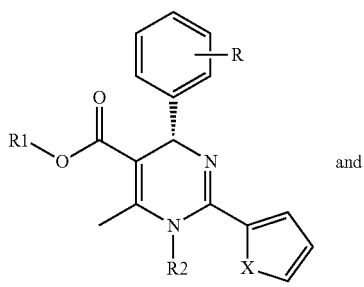

and

(VIII)

wherein R and $R^1$ are defined as above, and $R^2$ represents an acyl or sulphonic group containing at least one chiral center; and 2) reacting a compound of the formula (VII) or (VIII) with a strong base such as a sodium alkoxide in an appropriate solvent to obtain a pair of enantiomers of the compound of formula (I):

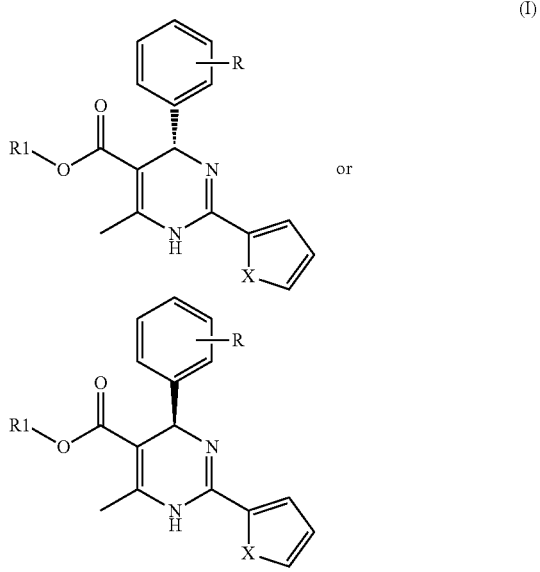

(I)

or wherein R and $R^1$ are defined as above.

The acid containing at least one chiral center in its molecule includes but is not limited to R- or S-configuration of camphanic acid and camphorsulfonic acid, D or L-configuration of tartaric acid, lactic acid and malic acid, natural or non-natural amino acids and derivatives thereof.

The condensing agent includes but is not limited to dicyclohexylcarbodiimide (DCC), diiso-propylcarbodiimide (DIC), N,N'-carbonyldiimidazole (CDI), 1-ethyl-3-[3-(dimethylamino)propyl]carbodiimide (EDCI), BOP (Castro condensing agent) and the like.

Or

Process [B] Comprising:

1) reacting a chiral primary amine $R^3R^4R^5CNH_2$ with diketene or diketene acetone adduct in the an inert solvent, with or without addition of a base, to obtain a compound represented by the formula (IX)

$$CH_3COCH_2CONHCR^3R^4R^5 \qquad (IX),$$

wherein $R^3$, $R^4$ and $R^5$ are any different substituents;

2) reacting an amidine of the formula (II) or a salt thereof,

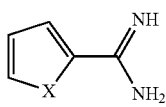
(II)

wherein X is defined as above, with an aldehyde of the formula (III),

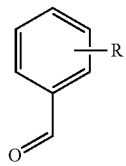
(III)

wherein R is defined as above, and a compound of the formula (IX) $CH_3COCH_2CONHCR^3R^4R^5$, in an appropriate inert solvent, with or without addition of a base or acid, to obtain a pair of diastereomers (X) and (XI) which are easy to be separated,

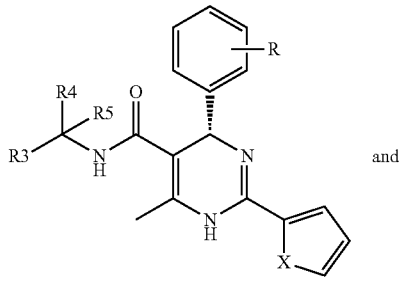
(X)

and

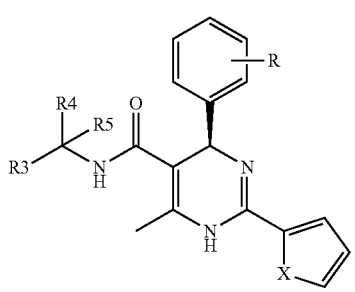
(XI)

wherein X, R, $R^3$, $R^4$ and $R^5$ are defined as above; and 3) acylating a compound of the formula (X) or (XI) in an insert solvent, then nitrosyling in an appropriate solvent, and reacting with an sodium alkoxide $R^1ONa$ to obtain a pair of enantiomers of a compound of formula (I):

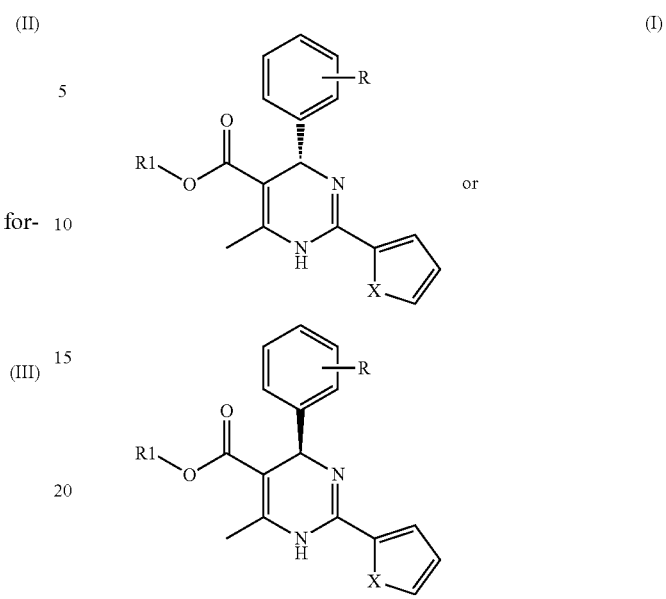
(I)

or

The chiral primary amine refers to a primary amine containing at least one chiral center in its molecule and may be R- or S-configuration, which includes but is not limited to (R)- or (S)-1-phenylethylamine, (R)- or (S)-1-phenyl propylamine, (R)- or (S)-1-(2-naphthyl)ethylamine, D- or L-natural or non-natural amino acids.

The chiral resolution processes of the compounds of the present application are illustrated using the following schemes as examples:

[A]

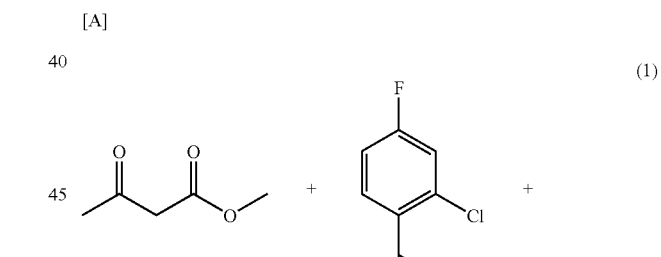
(1)

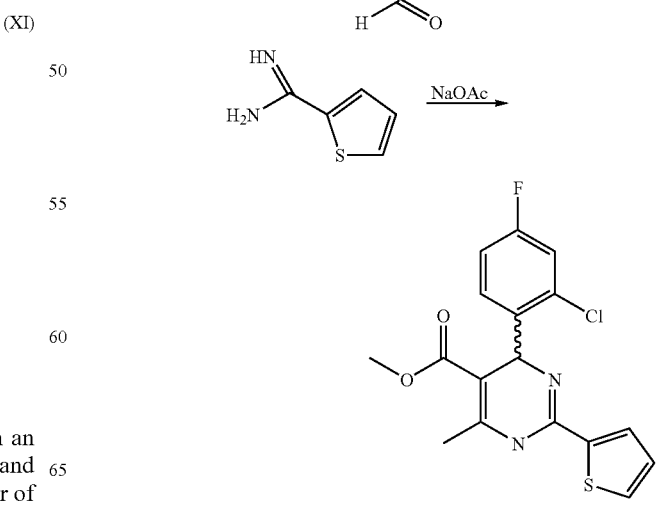

7
-continued
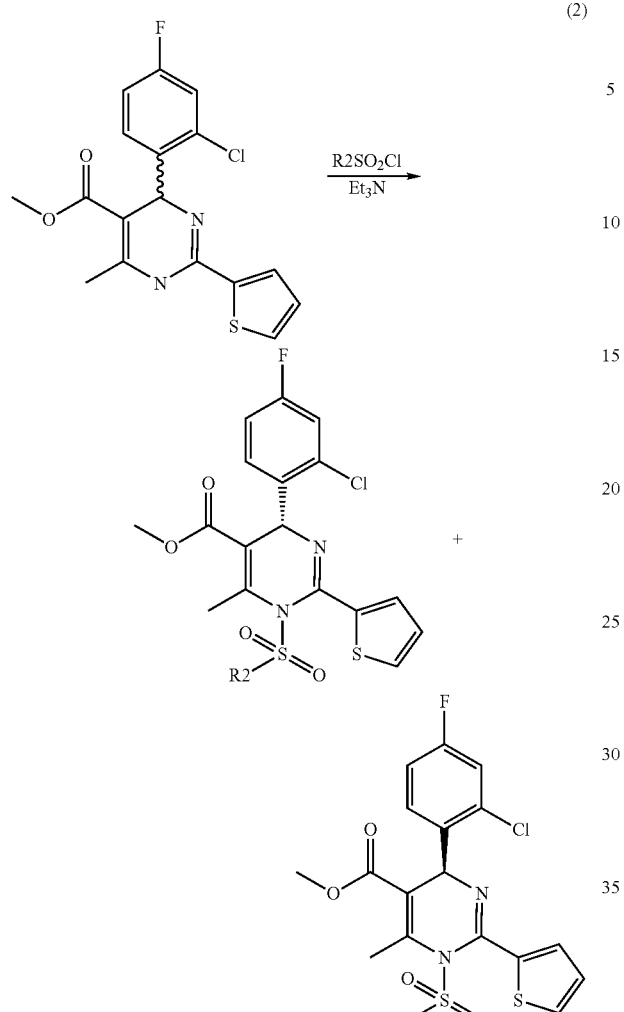
(2)
8
-continued
R2 =
[B]
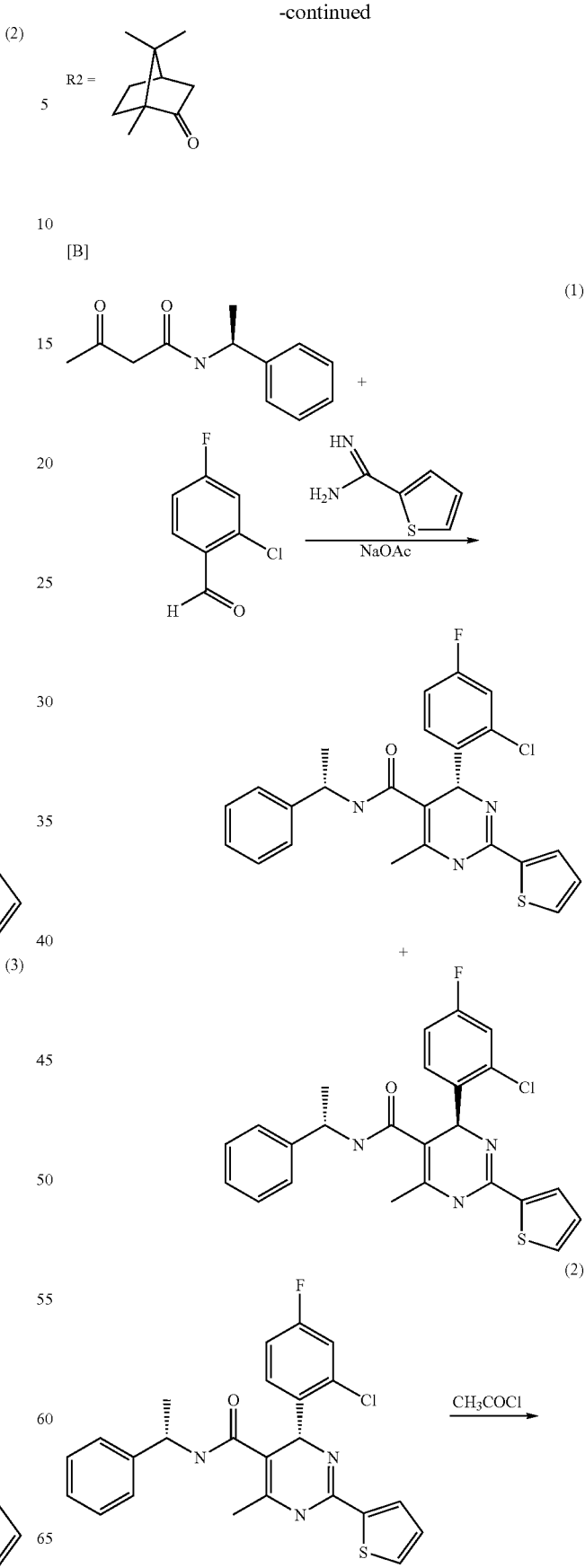

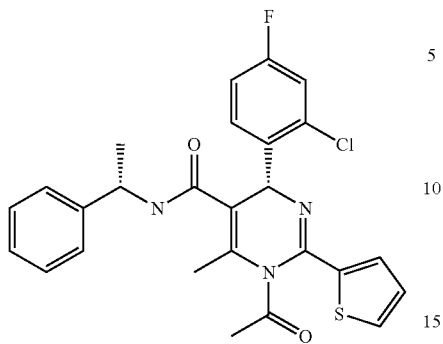

(3)

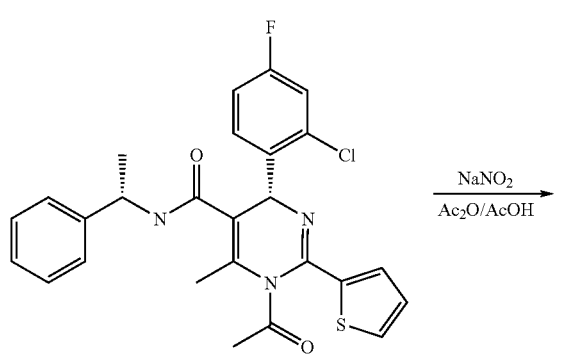

NaNO₂
—————→
Ac₂O/AcOH (4)

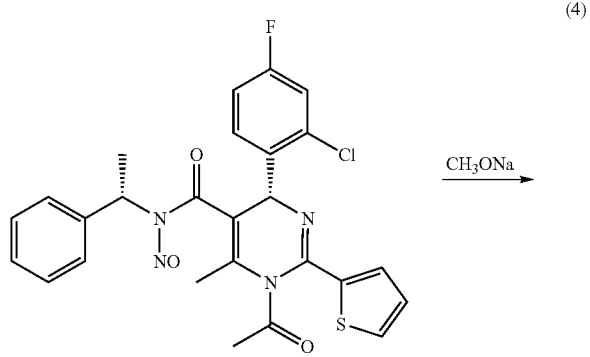

CH₃ONa
—————→

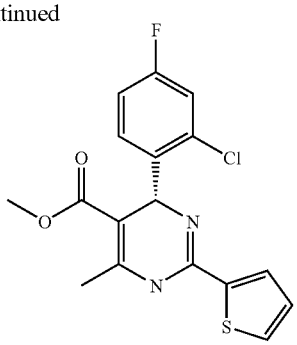

The compounds according to the present invention may also be present as salts, and the preference is given to pharmaceutically acceptable salts thereof.

The pharmaceutically acceptable salts include but are not limited to the salts of the compounds according to the present invention with inorganic acids such as hydrochloric acid, sulfuric acid, phosphoric acid, phosphorous acid hydrobromic acid and nitric acid, or with various organic acids such as maleic acid, fumaric acid, malic acid, furmaric acid, succinic acid, tartaric acid, citric acid, acetic acid, lactic acid, benzoic acid, methanesulphonic acid, ethanesulphonic acid, phenylsulphonic acid, para-toluenesulphomic acid or palmitic acid.

The pharmaceutically acceptable salts can also include but are not limited to the metal salts of the compounds according to the present invention, such as sodium, potassium, magnesium or calcium salts, or the ammonium salts formed with ammonia or an organic amine such as ethylamine, diethylamine, triethylamine, diethanolamine, triethanolamine, dicyclohexylamine, dimethylaminoethanol, arginine, lysine, ethylenediamine or 2-phenylethylamine.

Some compounds according to the present invention may be crystallized or recrystallized from water or various organic solvents. Under this circumstance, it is possible to form various solvates. The present invention includes stoichiometric solvates, including hydrates and compounds containing variable content of water formed during the preparation by lyophilization.

Preference is given to compounds of the formula (I) or isomers thereof, and salts or hydrates thereof, in which:
R represents one or more occurrences of identical or different substituents selected from the group consisting of hydrogen, halogen, cyano, carboxyl, hydroxyl, methyl and methoxy,
$R^1$ represents methyl, ethyl, n-propyl or iso-propyl, and
X represents oxygen or sulfur.

Very particular preference is given to compounds of the formula (I) or isomers thereof and salts or hydrates thereof, in which:
R represents one or more occurrences of identical or different substituents selected from the group consisting of hydrogen, fluorine and chlorine,
$R^1$ represents methyl or ethyl,
X represents oxygen or sulfur.

Particularly preferred compounds of the formula (I) according to the present invention are selected from the group consisting of:
(1) Methyl 2-(thien-2-yl)-4-(2-chloro-4-fluorophenyl)-6-methyl-1,4-dihyropyrimidin-5-carboxylate,
(2) Methyl 2-(furan-2-yl)-4-(2-chloro-4-fluorophenyl)-6-methyl-1,4-dihyropyrimidin-5-carboxylate,
(3) Ethyl 2-(thien-2-yl)-4-(2-chlorophenyl)-6-methyl-1,4-dihyropyrimidin-5-carboxylate (4) Methyl 2-(thien-2-yl)-4-phenyl-6-methyl-1,4-dihyropyrimidin-5-carboxylate,
(5) Ethyl 2-(furan-2-yl)-4-(2-chloro-4-fluorophenyl)-6-methyl-1,4-dihyropyrimidin-5-carboxylate,
(6) Methyl 2-(thien-2-yl)-4-(2-chlorophenyl)-6-methyl-1,4-dihyropyrimidin-5-carboxylate,
(7) Methyl 2-(thien-2-yl)-4-(4-fluorophenyl)-6-methyl-1,4-dihyropyrimidin-5-carboxylate,
(8) Ethyl 2-(furan-2-yl)-4-(2-chlorophenyl)-6-methyl-1,4-dihyropyrimidin-5-carboxylate,
(9) Ethyl 2-(furan-2-yl)-4-(4-fluorophenyl)-6-methyl-1,4-dihyropyrimidin-5-carboxylate,
(10) Ethyl 2-(furan-2-yl)-4-phenyl-6-methyl-1,4-dihyropyrimidin-5-carboxylate, and
(11) Ethyl 2-(thien-2-yl)-4-(2-chlorophenyl)-6-methyl-1,4-dihyropyrimidin-5-carboxylate,
or isomers thereof, and salts or hydrates thereof.

The compounds of the formula (I) according to the present invention can be prepared by:
A) reacting an amidine of the formula (II) or a salt thereof,

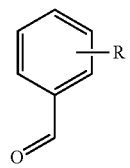
(II)

wherein X is defined as above, with an aldehyde of the formula (III),

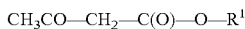
(III)

wherein R is defined as above, and a compound of the formula (IV)

CH$_3$CO—CH$_2$—C(O)—O—R$^1$    (IV), wherein R$^1$ is defined as above, in an appropriate inert solvent, with or without addition of a base or acid,
or
B) reacting a compound of the formula (V) or (VI),

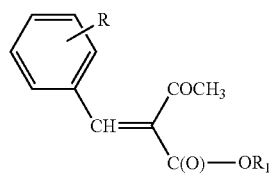
(V)

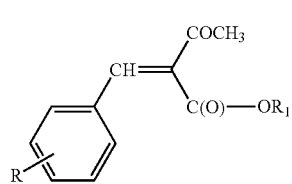
(VI)

In which R and R$^1$ are defined as above, with a compound of the formula (II), in an appropriate inert solvent, with or without addition of a base or acid, at a temperature of 10-150° C.

The processes according to the present invention can be illustrated by the following schemes:

[A]

[B]

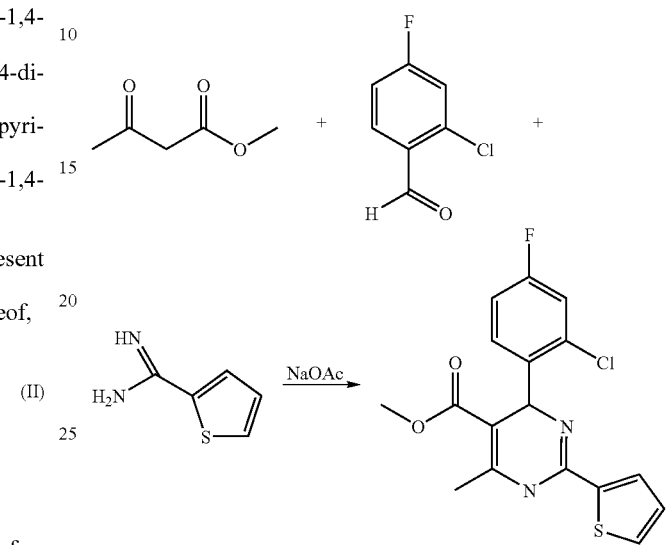

Solvents suitable for all schemes of [A] and [B] are any inert organic solvents. These solvents preferably include alcohols, such as ethanol, methanol, iso-propanol, ethers such as dioxane, ethyl ether, tetrahydrofuran, glycol monomethyl ether, glycol dimethyl ether or glacial acetic acid, dimethyl formamide, dimethyl sulphoxide, acetonitrile, pyridine and hexamethylphosphoramide.

The reaction temperature can be varied within a relatively wide range. In general, the reaction is carried out at a temperature between 20 and 150° C., but preferably at the boiling point of the respective solvent.

The reaction can be carried out at atmospheric pressure, or else at an elevated pressure. In general, the reaction is carried out at atmospheric pressure.

The reaction can be carried out with or without addition of a base or acid, The organic acids are, for example, formic acid, glacial acetic acid, methanesulphonic acid and para-toluenesulphonic acid, and the inorganic acids are, for example, hydrochloric acid, sulfuric acid, phosphoric acid and nitric acid. However, it is preferred that the reaction according to the present invention is carried out in the presence of a relatively weak acid, such as acetic acid or formic acid.

Bases suitable for the reaction preferably include organic bases such as triethylamine, methyldiethylamine, pyridine, hexahydropyridine and morpholine, and inorganic bases such as sodium carbonate, potassium carbonate, sodium hydrogen carbonate, sodium acetate, sodium hydroxide and potassium hydroxide.

The amidines of the formula (II) used as starting materials can be prepared from the corresponding cyano compounds by the methods known from the literatures (cf. Diana, G. D., Yarinsky, A., Zalay, E. S., et al, J. Med. Chem., 1969, 12(9): 791-793; Boere, R. J., Oakley, R. T, Read, R. V., J. Organometal. Chem., 1987, 331: 161-167; Judikins, B. D., Allen, D. g., Cook, T A., Synth. Commun., 1996, 26(23): 4351-4367).

The aldehydes of the formula (III) used as starting materials are known or can be prepared by methods known from the literatures (cf. T. D. Harris and G. P. Roth, J. Org. Chem., 1979, 44: 1446; DE 2165260, July 1972; DE2401665, July 1974; Mijano et. Al, CA 1963, 59, 13929c; E. Adler, H. D. Becker, Chem. Scand., 1961, 15, 849; E. P. Papadopoulos, M. Mardin, Ch. Issidoridis, J. Org. Chem. Sco., 1956, 78, 2543).

The ylidene-β-keto esters of the formula (V) or (VI) used as starting materials can be prepared from the aldehydes of the formula (III) and the compounds of the formula (IV) by methods known in the literature (cf. G. Jones., "The Knoevenagel Condensation", in Organic Reactions, Vol. XV, 204 ff. (1967)).

The compounds according to the present invention can be individually synthesized by conventional methods, or synthesized in the form of libraries (each library comprises at least two, or from 5 to 1000, more preferably from 10 to 100, of compounds) by mix-split or parallel synthesis process in combinatorial chemistry. That is to say, the compounds according to the present invention can be synthesized in liquid phase or solid phase.

More detailed information on the preparation of the compounds of formula I are provided in the following examples.

The antiviral activity of the compounds according to the present invention was determined by the methods described by Sells et al. (M. A. Sells, M. L. Chen, g. Acs, Proc. Natl. Acad. Sci., 1987, 84, 1005-1009) and Korba et al., (B. E. Korba, J. L. Gerin, Antiviral Research, 1992, 19. 55-70).

The antiviral tests were carried out in 96-well microtiter plates. Only growth medium and HepG 2.2.15 cells were added to the first vertical row of the plate as a blank control.

Stock solutions of the test compounds (50 mM) were first dissolved in DMSO, and further dilutions were prepared in the growth medium of HepG 2.2.15 cell. The compounds according to the present invention, usually in a test concentration of 100 μg/ml ($1^{st}$ test concentration), were pipetted into each well of the second vertical test row of the microtiter plate and subsequently diluted with growth medium plus 2% of foetal calf serum (volume 25 μl) by 2 fold each time, up to $2^{10}$-fold.

225 μl of a HepG 2.2.15 cell suspension ($5 \times 10^4$ cells/ml) in growth medium plus 2% foetal calf serum were then added to each well of the 96-well microtiter plate.

The test mixture was incubated at 37° C., 5% $CO_2$ for 4 days. The supernatant was subsequently siphoned off and discarded, and 225 μl of freshly prepared growth medium were added to each well. The compounds according to the present invention were added again in a volume 25 μl. The mixture were incubated from another 4 days.

Before the supernatants were harvested for determining the antiviral effect, the HepG 2.2.15 cells were examined under the optical microscopy or by biochemical detecting methods (for example Alamar Blue staining or Trypan Blue staining) for cytotoxic changes.

The supernatants were subsequently harvested and siphoned in vacuum onto 96-well dot blot chambers covered with a nylon membrane (in accordance with the instructions of the manufacturer).

Determination of the Cytotoxicity

Substances-induced cytotoxic or cytostatic changes in HepG 2.2.15 cells were determined as changes in the cell morphology, for example under an optical microscope. Such substance-induced changes in the HepG 2.2.15 cells in comparison with untreated cells was apparent, for example cell lysis, vacuolization or changed cell morphology. The pathological changes were observed under a microscope after 8 days as indices with complete destroy being designated as 4, 75% as 3, 50% as 2, 25% as 1, and no pathological change as 0. The average degree of the pathological change and percent inhibition at each concentration were calculated, and a half-maximum toxic concentration ($TC_{50}$) and a maximum non-toxic concentration $TC_0$ were determined according to Reed & Muench methods.

$TC_{50}$ means the concentration of the compounds according to the present invention at which 50% of the cells have a morphology similar to the corresponding cell control.

Determination of the Antiviral Activity

After transfer of the supernatants onto the nylon membrane of the blot apparatus (see above), the supernatants of the HepG 2.2.15 cells were denatured (1.5 M NaCl/0.5 N NaOH), neutralized (3 M NaI/0.5 M Tris HCl, pH 7.5) and washed (2×SSC). By incubation of the filter membrane at 120° C. for 2-4 hours, the DNA was subsequently baked onto the membrane.

Hybridization of the DNA

The viral DNA of the treated HepG 2.2.15 cells on the nylon filter membrane was usually determined using non-radioactive digoxigenin-labelled hepatitis B-specific DNA probes which were in each case labelled with digoxigenin, purified and used for hybridization in accordance with the instructions of the manufacturer.

Briefly speaking, the prehybridization and hybridization were carried out in 5×SSC, 1× blocking agent, 0.1% N-lauroylsacosine, 0.02% SDS and 100 μg of DNA from herring sperm. The prehybridization was carried out at 60° C. for 30 minutes and the specific hybridization was carried out using 20 to 40 ng/ml of the digoxigeninated denatured HBV-specific DNA (14 hours, 60° C.). The filler membrane was subsequently washed and the antibodies against digoxigenin of HBV DNA were determined.

The digoxigenin-labeled DNA was detected immunologically in accordance with the instructions of the manufacturer.

Briefly speaking, the filler membrane were washed and prehybridized with a blocking agent (in accordance with the instructions of the manufacturer). They were subsequently hybridized for 30 minutes using an anti-DIG antibody previously coupled to alkaline phosphatase. After washing, the substrate of alkaline phosphatase, CSPD, was added, incubated with the filters for 5 minutes, subsequently wrapped in plastic film and incubated at 37° C. for a further 15 minutes. The chemiluminescent signals of the Hepatitis B-specific DNA were measured by exposing of the filters to an X-ray film (incubation for 10 minutes to 2 hours depending on the signal strength) to determine the half-maximum inhibitory concentration ($IC_{50}$).

The half-maximum inhibitory concentration ($IC_{50}$) means the concentration of the compound according to the present invention at which the hepatitis B-specific band was reduced by 50% in comparison with an untreated sample.

The compounds according to the present invention exhibited a relatively strong antivirus activity. Although the compound in Example 1 is similar in structure to the compound in Example 4, they differ from each other in antiviral activity by thousands times due to modification of the substituents. Since such compounds are surprisingly active against hepatitis B (HBV), they are therefore useful for treating the virus-induced diseases, in particular acute and chronically persisting diseases caused by HBV virus infection. A chronic viral disease caused by HBV can lead to different severity of various complex symptoms. It is well known that chronic hepatitis B virus infection may result in cirrhosis of the liver and/or hepatocellular carcinoma.

Examples of indications for which the compounds according to the present invention can be used to treat are:

The treatment of acute and chronic virus infections which may lead to an infectious hepatitis, for example, infections with hepatitis B viruses Particular preference is given to the treatment of chronic hepatitis B infections and the treatment of acute hepatitis B virus infection.

The pharmaceutical composition comprising the compound of the present invention can be administered by any one of following routes: oral, spray inhalation, rectal, nasal cavity, vaginal, topical, parenteral, such as subcutaneous, intravenous, intramuscular, intraperitoneally, intrathecal, intraventricular, intrasternal or intracel injection or importation, or administered by means of an explanted reservoir, preferably oral administration, intramuscular injection, intraperitoneral or intravenous administration.

The compound according to the present invention or a pharmaceutical composition comprising the compound of the present invention can be administered in unit dose form. Administration dosage form can be a liquid or solid dosage form. The liquid dosage form can be true solutions, colloids, particulates, emulsions, suspensions. Other dosage forms include, e.g., tablets, capsules, drop pills, aerosols, pills, powders, solutions, suspensions, emulsions, granulates, suppositories, lyophilized powders, clathrates, implants, patches, embrocations, and so on.

The pharmaceutical composition of the present invention further comprises pharmaceutically acceptable carriers, herein the pharmaceutically acceptable carriers include but are not limited to: ion exchangers, alumina, aluminum stearate, lecithin, serum protein such as human serum protein, buffers such as phosphate, glycerol, sorbic acid, potassium sorbate, partial glycerolipid mixtures of saturated vegetable fatty acids, water, salts or electrolytes, such as potamine sulfate, disodium hydrogen phosphate, potassium hydrogen phosphate, sodium chloride, zinc salts, colloidal silica, magnesiu, trisilicate, polyvinylpyrrolidone, cellulose materials, polyglycol, carboxylmethylcellulose sodium, polyacrylate, beeswax, lanolin, and so on. The content of carriers in the pharmaceutical composition can be 1% to 98% by weight, generally about 80% by weight. For convenience, topical anesthetic, preservative and buffer, etc. can be directly dissolved in the carriers.

Oral tablets and capsules can contain excipients, such as binders, e.g., syrup, gum Arabic, sorbitol, bassora gum, or polyvinyl pyrrolidone, fillers, e.g., lactose, sucrose, corn starch, calcium phosphate, sorbitol, animoacetic acid, lubricants, e.g., magnesium stearate, talc, polyglycol, silica, disintegrants, e.g., potato starch, or pharmaceutically acceptable wetting agents, such as sodium lauryl sulfate. The tablets can be coated by the methods known in the field of pharmaceutics.

Oral liquids can be prepared into suspensions of water and oil, solutions, emulsions, syrups or elixirs, and can also be prepared into dried products, which are supplied with water or other suitable vehicle before use. This liquid formulation can contain routine additives, such as a suspending agent, sorbitol, cellulose methyl ether, glucose syrup, gel, hydroxyethylcelulose, carboxylmethylcellulose, aluminum stearate gel, hydrogenated edible fats, emulsifiers, such as lecithin, Span-80, Arabic gum; or non-aqueous carriers (which may contain edible oils), such as almond oil, fats, such as glycerol, ethylene glycol, or ethanol; preservatives, such as methyl p-hydroxybenzoate or propyl p-hydroxybenzoate, sorbic acid. If required, flavoring agents or coloring agents can be added.

Suppositories can contain routine suppository, such as cocoa butter or other glycerides.

For parenteral administration, liquid dosage forms are usually formulated from a compound and a sterile carrier. The carrier is principally selected from water. According to the difference of the carrier selected and the concentration of pharmaceutical, the compound can be dissolved into the carrier and prepared into a suspension. When an injection solution is prepared, the compound is dissolved into water, then filtrated, disinfected and packed into seal bottle or ampoule.

When administrated topically to the skin, the compounds according to the present invention can be prepared into a suitable form of ointment, lotion, or cream, in which the active ingredient is suspended or dissolved into one or more carriers. The carrier for use in ointment formulation includes but is not limited to mineral oil, liquid paraffin, white paraffin, propanediol, polyethylene oxide, polyoxytrimethylene, emulsifying wax and water; the carrier for use in lotion and cream includes but is not limited to mineral oil, sorbitan monostearate, Tween-60, cetearyl ester wax, hexadecylene aromatic alcohol, 2-octyldodecanol, benzyl alcohol and water.

In the abovementioned pharmaceutical formulations, the active compounds of the formula (I) should be present in a concentration of approximately from 0.1 to 99.5% by weight, preferably of approximately from 0.5 to 95% by weight of the total mixture.

The abovementioned pharmaceutical formulations may, in addition to the compounds of the formula I, comprise further pharmaceutically active compounds.

In general, it has been proved to be advantageous both in human and veterinary medicine to administer the active compound(s) in total amounts of from about 0.5 to 500 mg, preferably from 1 to 100 mg/kg of body weight per 24 hours, if appropriate in the form of multiple unit doses, to obtain the desired results. A unit dose preferably contains the active compound(s) in amounts of from about 1 to 80 mg, more preferably from 1 to 50 mg/kg of body weight. However, it may be necessary to deviate from the specified dosages, depending on the nature and the body weight of the subject to be treated, the nature and the severity of the disease, the formulation type and the administration of the medicament, and the time or interval within which administration is carried out.

CONCRETE MODES FOR CARRYING OUT THE INVENTION

Following specific examples are preferred embodiments of the present invention, which should not be understood to form a restriction to the present invention in any way.

The melting point of the compounds was determined by RY-1 melting point apparatus, and the thermometer was not revised. The mass spectrum of the compounds was determined using Micromass ZabSpec high resolution (a resolution of 1000) mass spectroscope. The $^1$H-NMR of the compounds was determined using JNM-ECA-400 superconductive NMR instrument, frequency of operation is $^1$H-NMR 400 MHz, and $^{13}$C-NMR 100 MHz.

EXAMPLES

Example 1

Preparation of methyl 2-(thien-2-yl)-4-(2-chloro-4-fluorophenyl)-6-methyl-1,4-dihyropyrimidin-5-carboxylate

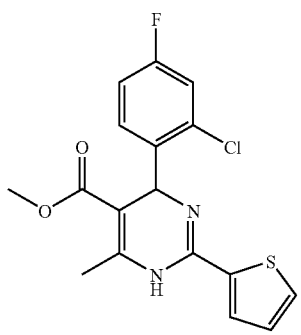

2.164 mmol of 2-thienylformamidine hydrochloride (Schaefer F. C., Peters G. A., et al, J. Org. Chem.; 1961, 26(2): 412-418), 2.164 mmol of 2-chloro-4-fluorobenzaldehyde, 2.164 mmol of methyl acetoacetate and 2.2 mmol of sodium acetate in 10 ml of anhydrous ethanol was reacted under reflux for 20 hours and concentrated. Ethyl acetate and water were added to the reaction, and the phases were separated. The ethyl acetate layer was dried over anhydrous sodium sulfate and separated by a column chromatography to give 0.22 g of a yellow crystal (yield: 30%); $^1$H-NMR (400 MHz, CDCl$_3$) δ 2.55 (3H, s, CH$_3$); 3.62 (3H, s, CH$_3$); 6.00 (1H, s, CH); 6.89-6.94 (1H, m, ArH); 7.03-7.05 (1H, dd, J$_1$=4.80 Hz, J$_2$=3.60 Hz, ArH); 7.11-7.14 (1H, m, ArH); 7.26-7.30 (1H, m, ArH); 7.33-7.34 (1H, d, J$_2$=3.60 Hz, ArH); 7.44-7.45 (1H, d, J$_1$=4.80 Hz ArH); MS (HREI) 344.0448 (M$^+$).

Example 2

Preparation of methyl 2-(furan-2-yl)-4-(2-chloro-4-fluorophenyl)-6-methyl-1,4-dihyropyrimidin-5-carboxylate

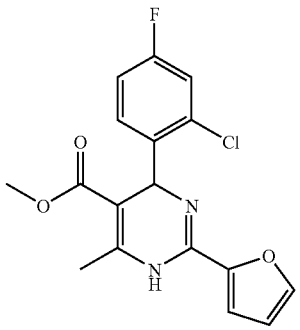

According to the process of Example 1, except that the 2-thienylformamidine hydrochloride was replaced by 2-furylformamidine hydrochloride, and 0.23 g of a pale yellow particulates were obtained (yield: 31%); $^1$H-NMR (400 MHz, DMSO-d$_6$) δ 2.32 (3H, s, CH$_3$); 3.51 (3H, s, CH$_3$); 5.50 (1H, s, CH); 6.59 (1H, m, ArH); 7.00-7.23 (4H, m, ArH); 7.78-7.83 (1H, m, ArH); 9.23-9.44 (1H, BR, NH). MS (EI) 346.2 (M$^+$).

Example 3

Preparation of ethyl 2-(thien-2-yl)-4-(2-chloro-4-fluorophenyl)-6-methyl-1,4-dihyropyrimidin-5-carboxylate

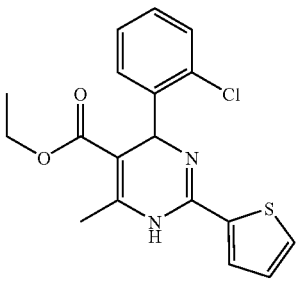

According to the process of Example 1, except that the 2-chloro-4-fluorobenzaldehyde and methyl acetoacetate were replaced by 2-chlorobenzaldehyde and ethyl acetoacetate, respectively, and 0.26 g of a pale yellow particulates were obtained (yield: 34%); $^1$H-NMR (400 MHz, CDCl$_3$) δ 1.13-1.15 (3H, t, J=7.0 Hz, CH$_3$); 2.57 (3H, s, CH$_3$); 4.04-4.07 (2H, m, J=7.0 Hz, CH$_2$) 6.07 (1H, s, CH); 7.02-7.04 (1H, m, ArH); 7.17-7.23 (2H, m, ArH); 7.32-7.39 (3H, m, ArH); 7.44-7.45 (1H, m, ArH). MS (HREI) 360.0698 (M$^+$).

Example 4

Preparation of methyl 2-(thien-2-yl)-4-phenyl-6-methyl-1,4-dihyropyrimidin-5-carboxylate

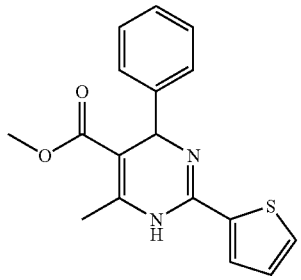

According to the process of Example 1, except that the 2-chloro-4-fluorobenzaldehyde was replaced by benzaldehyde, and 0.20 g of a pale yellow particulates were obtained (yield: 30%); $^1$H-NMR (400 MHz, CDCl$_3$) δ 2.45-2.46 (3H, s, CH$_3$); 3.66 (3H, s, CH$_3$); 5.68-5.90 (1H, s, CH); 7.04-7.07 (1H, m, ArH); 7.23-7.45 (6H, m, ArH). MS (FAB) 313.2 (M+1).

Example 5

Preparation of ethyl 2-(furan-2-yl)-4-(2-chloro-4-fluorophenyl)-6-methyl-1,4-dihyropyrimidin-5-carboxylate

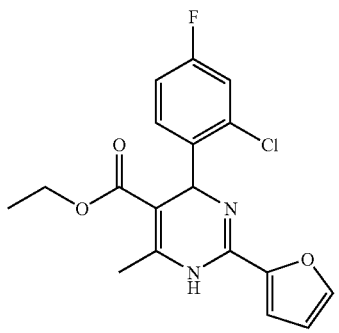

According to the process of Example 1, except that the 2-thienylformamidine hydrochloride and methyl acetoacetate were replaced by 2-furylformamidine hydrochloride and ethyl acetoacetate, respectively, and 0.22 g of a pale yellow particulates were obtained (yield: 29%); $^1$H-NMR (400 MHz, CDCl$_3$) δ 1.11-1.15 (3H, t, J=7.2 Hz, CH$_3$); 2.54 (3H, s, CH$_3$); 4.03-4.06 (2H, m, J=7.2 Hz, CH$_2$); 6.10 (1H, s, CH); 6.92-6.93 (1H, m, ArH); 7.10-7.13 (1H, m, ArH); 7.31-7.34 (1H, m, ArH); 7.46 (1H, s, ArH). MS (FAB) 363.2 (M+1).

Example 6

Preparation of methyl 2-(thien-2-yl)-4-(2-chlorophenyl)-6-methyl-1,4-dihyropyrimidin-5-carboxylate

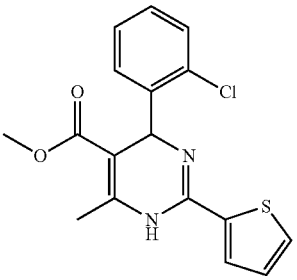

According to the process of Example 1, except that the 2-chloro-4-fluorobenzaldehyde was replaced by 2-chlorobenzaldehyde, and 0.20 g of a pale yellow particulates were obtained (yield: 30%); $^1$H-NMR (400 MHz, DMSO-d$_6$) δ 9.47 (s, 1H, NH); 7.80 (s, 1H, ArH); 7.62 (s, 1H, ArH); 7.41-7.39 (m, 1H, ArH), 7.30-7.21 (m, 3H, ArH); 7.11-7.09 (m, 1H, ArH); 5.92 (s, 1H, CH); 3.48 (s, 3H, CH$_3$); 2.44 (s, 3H, CH$_3$). MS (EI): 314.0 (M$^+$).

Example 7

Preparation of methyl 2-(thien-2-yl)-4-(4-fluorophenyl)-6-methyl-1,4-dihyropyrimidin-5-carboxylate

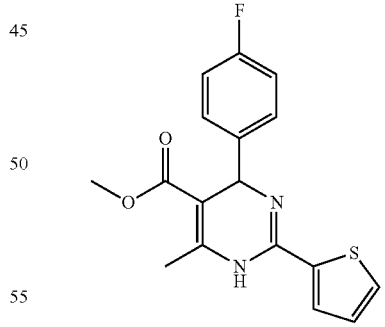

According to the process of Example 1, except that the 2-chloro-4-fluorobenzaldehyde was replaced by 4-fluorobenzaldehyde, and 0.22 g of a pale yellow particulates were obtained (yield: 21%); $^1$H-NMR (400 MHz, CDCl$_3$-d$_1$) δ 7.45-7.42 (m, 2H, ArH); 7.35-7.31 (t, 2H, J=8.8 Hz, ArH); 7.06-7.04 (m, 1H, ArH); 6.98-6.94 (t, 2H, J=8.8 Hz, ArH); 5.67 (s, 1H, CH); 3.66 (s, 3H, CH$_3$); 2.46 (s, 3H, CH$_3$); MS (EI) 330.1 (M$^+$).

Example 8

Preparation of ethyl 2-(furan-2-yl)-4-(2-chlorophenyl)-6-methyl-1,4-dihyropyrimidin-5-carboxylate

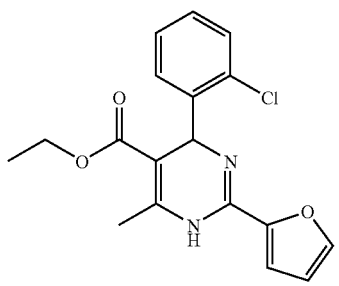

According to the process of Example 1, except that the 2-thienylformamidine hydrochloride, 2-chloro-4-fluorobenzaldehyde and methyl acetoacetate were replaced by 2-furylformamidine hydrochloride, 2-chlorobenzaldehyde and ethyl acetoacetate, respectively, and 0.20 g of a pale yellow particulates were obtained (yield: 28%); $^1$H-NMR (400 MHz, CDCl$_3$-d$_1$) δ 7.45 (s, 1H, ArH); 7.37-7.34 (m, 2H, ArH); 7.20-7.10 (m, 2H, ArH); 6.48 (m, 1H, ArH); 6.09 (s, 1H, CH); 4.07-4.03 (q, 2H, J=7.2 Hz, CH2); 2.55 (s, 3H, CH3); 1.13-1.09 (t, 3H, J=7.2 Hz, CH3). MS (EI) 344.0 (M$^+$).

Example 9

Preparation of ethyl 2-(furan-2-yl)-4-(4-fluorophenyl)-6-methyl-1,4-dihyropyrimidin-5-carboxylate

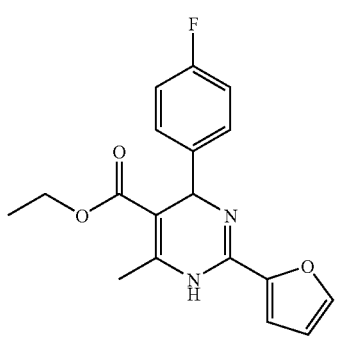

According to the process of Example 1, except that the 2-thienylformamidine hydrochloride, 2-chloro-4-fluorobenzaldehyde and methyl acetoacetate were replaced by 2-furylformamidine hydrochloride, 4-fluorobenzaldehyde and ethyl acetoacetate, respectively, and 0.21 g of a pale yellow particulates were obtained (yield: 29%); $^1$H-NMR (400 MHz, CDCl$_3$-d$_1$) δ 7.47-7.46 (d, 1H, J=1.2 Hz, ArH) 7.36-7.32 (t, 2H, J=8.8 Hz, ArH); 7.11 (s, 1H, ArH); 6.98-6.94 (t, 2H, J=8.8 Hz, ArH); 6.52-6.51 (q, 1H, J=1.4 Hz, ArH); 5.69 (s, 1H, CH); 4.12-4.10 (q, 2H, J=7.2 Hz, CH$_2$); 1.21-1.18 (t, 3H, J=7.6 Hz, CH$_3$). MS (EI) 328.1 (M$^+$).

Example 10

Preparation of ethyl 2-(furan-2-yl)-4-phenyl-6-methyl-1,4-dihyropyrimidin-5-carboxylate

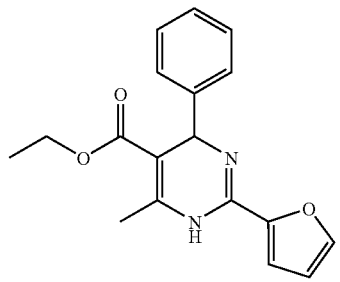

According to the process of Example 1, except that the 2-thienylformamidine hydrochloride, 2-chloro-4-fluorobenzaldehyde and methyl acetoacetate were replaced by 2-furylformamidine hydrochloride, benzaldehyde and ethyl acetoacetate, respectively, and 0.21 g of a pale yellow particulates were obtained (yield: 32%); $^1$H-NMR (400 MHz, CDCl$_3$-d$_1$) δ 7.45 (s, 1H, ArH); 7.39-7.37 (d, 2H, J=7.2 Hz, ArH); 7.30-7.21 (m, 3H, J=7.2 Hz, ArH); 7.09 (s, 1H, ArH); 6.50 (m, 1H, ArH), 5.71 (s, 1H, CH); 4.12-4.09 (q, 2H, J=7.2 Hz, CH2); 2.45 (s, 3H, CH3): 1.21-1.17 (t, 3H, J=7.2 Hz, CH3). MS (EI) 310.2 (M$^+$).

Example 11

Preparation of ethyl 2-(thien-2-yl)-4-(2-chlorophenyl)-6-methyl-1,4-dihyropyrimidin-5-carboxylate

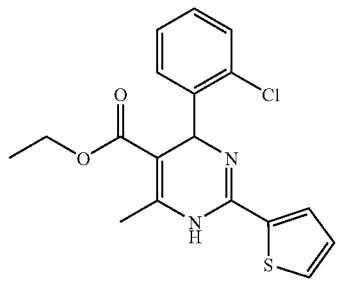

According to the process of Example 1, except that the 2-chloro-4-fluorobenzaldehyde and methyl acetoacetate were replaced by 2-chlorobenzaldehyde and ethyl acetoacetate, respectively, and 0.29 g of a pale yellow particulates were obtained (yield: 37%); $^1$H-NMR (400 MHz, CDCl$_3$-d$_1$) δ 7.45-7.44 (m, 1H, ArH); 7.39-7.32 (m, 3H, ArH); 7.23-7.17 (m, 2H, ArH); 7.04-7.02 (t, 1H, J=, 4.8 Hz, ArH); 6.07 (s, 1H, CH); 4.07-4.04 (q, 2H, J=7.2 Hz, ArH); 2.57 (s, 3H, CH$_3$): 1.15-1.31 (t, 3H, J=7.6 Hz, CH$_3$). HREI: 360.0698 (M$^+$).

Example 12

Determination of the Cytotoxicity and Antiviral Activity of the Compounds

The cytotoxicity and antiviral activity of the compounds according to the present invention were determined by the methods as described above, and the results were shown in Table 1.

TABLE 1

Inhibitory effects of the compounds on HBV DNA

| Example No. | IC$_{50}$ μM | TC$_{50}$ μM | SI |
|---|---|---|---|
| 1 | 0.007 | 1098.5 | >10$^5$ |
| 4 | 29.61 | 105.44 | 3.56 |

What is claimed is:

1. A compound selected from the group consisting of:
   (5) Ethyl 2-(furan-2-yl)-4-(2-chloro-4-fluorophenyl)-6-methyl-1,4-dihyropyrimidin-5-carboxylate,
   (8) Ethyl 2-(furan-2-yl)-4-(2-chlorophenyl)-6-methyl-1,4-dihyropyrimidin-5-carboxylate,
   (9) Ethyl 2-(furan-2-yl)-4-(4-fluorophenyl)-6-methyl-1,4-dihyropyrimidin-5-carboxylate,
   (10) Ethyl 2-(furan-2-yl)-4-phenyl-6-methyl-1,4-dihyropyrimidin-5-carboxylate
   (11) Ethyl 2-(thien-2-yl)-4-(2-chlorophenyl)-6-methyl-1,4-dihyropyrimidin-5-carboxylate,
   and pharmaceutically acceptable salts thereof.

2. A process for the preparation of a compound of formula (I)

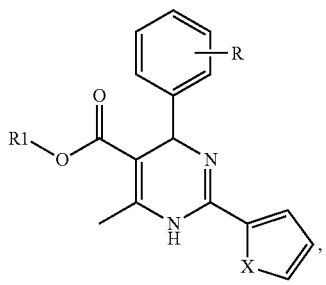
(I)

wherein R represents one or more occurrences of identical or different substituents selected from the group consisting of hydrogen, halogen, trifluoromethyl, trifluoromethoxy, trifluoromesyl, nitro, cyano, carboxyl, hydroxyl, (C$_1$-C$_6$)-alkoxy, (C$_1$-C$_6$)-alkoxycarbonyl or (C$_1$-C$_6$)-alkyl, R$^1$ represents a (C$_2$-C$_6$)-alkyl group, and X represents oxygen or sulfur, or an optical or tautomeric isomer or a pharmaceutically acceptable salt thereof;

said process comprising:

A) reacting an amidine of the formula (II) or a salt thereof,

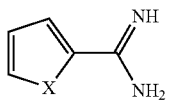
(II)

wherein X is defined as above, with an aldehyde of the formula (III),

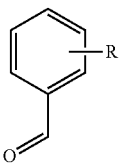
(III)

wherein R is defined as above, and a compound of the formula (IV)

$$CH_3CO-CH_2-C(O)-O-R^1 \quad (IV),$$

wherein R$^1$ is defined as above, in an appropriate inert solvent selected from the group consisting of ethanol, methanol, iso-propanol, dioxane, ethyl ether, tetrahydrofuran, glycol monomethyl ether, glycol dimethyl ether, glacial acetic acid, dimethyl formamide, dimethly sulphoxide, acetonitrile, pyridine and hexamethylphosphoramide, with or without addition of a base or acid, or B) reacting a compound of the formula (V) or (VI),

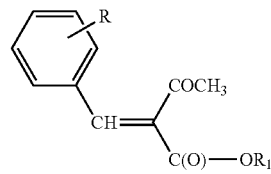
(V)

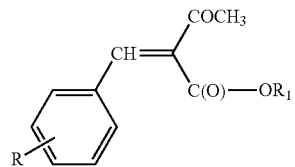
(VI)

wherein R and R$^1$ are defined as above, with a compound of the formula (II), in an appropriate inert solvent selected from the group consisting of ethanol, methanol, iso-propanol, dioxane, ethyl ether, tetrahydrofuran, glycol monomethyl ether, glycol dimethyl ether, glacial acetic acid, dimethyl formamide, dimethyl sulphoxide, acetonitrile, pyridine and hexamethylphosphoramide, with or without addition of a base or acid.

* * * * *